United States Patent [19]

Von Der Saal et al.

[11] Patent Number: 5,019,587

[45] Date of Patent: May 28, 1991

[54] BICYCLIC CARBOXAMIDES, COMPOSITIONS CONTAINING SAME AND USE THEREOF

[75] Inventors: Wolfgang V. Von Der Saal, Weinheim; Alfred Mertens, Schriesheim; Erwin Boehm, Mannheim, all of Fed. Rep. of Germany

[73] Assignee: Boehringer Mannheim GmbH, Mannheim, Fed. Rep. of Germany

[21] Appl. No.: 361,090

[22] Filed: Jun. 5, 1989

[30] Foreign Application Priority Data

Jun. 3, 1988 [DE] Fed. Rep. of Germany ....... 3818830

[51] Int. Cl.$^5$ .................. C07D 209/34; C07D 405/12; A61K 31/40
[52] U.S. Cl. .................... 514/409; 514/414; 514/418; 548/411; 548/454; 548/486
[58] Field of Search .................. 548/486, 411, 454; 514/418, 409, 414

[56] References Cited

U.S. PATENT DOCUMENTS 4,468,402  8/1984  Tominaga et al. ............ 514/312
4,791,109 12/1988  Clemence et al. ............ 548/486

FOREIGN PATENT DOCUMENTS

0236140A2  9/1987  European Pat. Off. .
0255134A2  2/1988  European Pat. Off. .
3204892A1  9/1982  Fed. Rep. of Germany .

Primary Examiner—Robert W. Ramsuer
Assistant Examiner—Lenora Miltenberger
Attorney, Agent, or Firm—Armstrong, Nikaido, Marmelstein, Kubovcik & Murray

[57] ABSTRACT

The present invention provides compounds of the general formula (I) which inhibit the aggregation of erythrocytes or thrombocytes

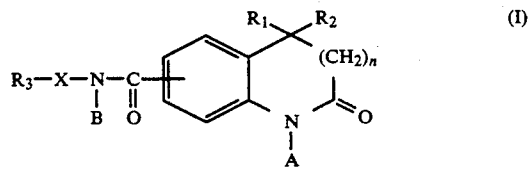

wherein A is hydrogen or $C_1$–$C_6$-alkyl, $C_2$–$C_6$-alkenyl, $C_2$–$C_6$-alkynyl, benzyl or $C_3$–$C_7$-cycloalkyl radical, B is hydrogen, $R_1$ is a $C_1$–$C_6$-alkyl, $C_2$–$C_6$-alkenyl or $C_3$–$C_7$-cycloalkyl radical, $R_2$ is a $C_1$–$C_6$-alkyl, $C_2$–$C_6$-alkenyl, $C_3$–$C_7$-cycloalkyl, $C_1$–$C_6$-alkylcarbonyl, $C_1$–$C_6$-alkoxycarbonyl, aminocarbonyl or hydrazinocarbonyl radical, or $R_1$ and $R_2$, together with the carbon atom to which they are attached, form a $C_3$–$C_7$-cycloalkyl ring, n is 0, X is a valency bond or a $C_1$–$C_6$-alkylene radical, $R_3$ is a carbocyclic aromatic ring, which may be substituted; and the tautomers, optically-active forms and physiologically acceptable salts thereof with organic and inorganic acids.

10 Claims, No Drawings

BICYCLIC CARBOXAMIDES, COMPOSITIONS CONTAINING SAME AND USE THEREOF

The present invention is concerned with new bicyclic carboxamides, processes for the preparation thereof and pharmaceutical compositions containing them.

The new bicyclic carboxamides according to the present invention are compounds of the general formula:

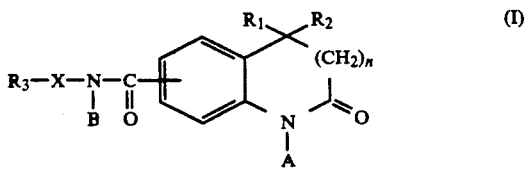

wherein A and B, which can be the same or different, are hydrogen atoms or alkyl, alkenyl, alkynyl, benzyl or cycloalkyl radicals, $R_1$ is a hydrogen atom or an alkyl, alkenyl or cycloalkyl radical, $R_2$ is a hydrogen atom or an-alkyl, alkenyl, cycloalkyl, alkylcarbonyl, alkoxycarbonyl, aminocarbonyl or hydrazinocarbonyl radical or $R_1$ and $R_2$, together with the carbon atom to which they are attached, form a cycloalkyl radical, n is 0 or 1, X is a valency bond or an alkylene radical, $R_3$ is an aromatic heterocyclic five- or six-membered ring containing 1 to 4 heteroatoms, the heteroatoms being the same or different and being oxygen, sulphur or nitrogen atoms which, if desired, can carry an oxygen atom on one or more nitrogen atoms and the six-membered ring can, if desired, be substituted by a pyridinyloxy or phenyloxy radical or the five- or six-membered ring can be condensed with a phenyl ring or an aromatic five- or six-membered ring containing 1 to 4 heteroatoms to form a bicyclic radical and, if desired, the five- and six-membered ring, the bicyclic radicals, the pyridinyloxy and the phenoyloxy radical can be substituted one or more times by alkyl, alkoxy, alkenyloxy, alkoxycarbonyl, carboxyl, alkylthio, hydroxyl, nitro, amino, halogen or cyano or $R_3$ is a phenyl radical of the general formula:

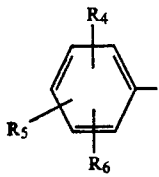

wherein $R_4$, $R_5$ and $R_6$, which can be the same or different, are hydrogen atoms, imidazolyl radicals, oxypyridazinyl radicals optionally substituted with alkyl radicals, which, if desired, can be hydrogenated, alkanesulphonyloxy, trifluoromethanesulphonyloxy, phenylsulphonylamino, alkanesulphonylamino, trifluoromethanesulphonylamino, N-alkyl-alkanesulphonylamino, N-alkyltrifluoromethanesulphonylamino, alkylsulphenylmethyl, alkylsulphinylmethyl, or alkylsulphonylmethyl radicals, carbonyl groups substituted by hydroxyl, alkoxy, amino, alkylamino or dialkylamino, sulphonyl groups substituted by amino, alkylamino, dialkylamino, piperidino or morpholino, alkylcarbonylamino, aminocarbonylamino, alkylaminocarbonylamino, alkylthio, alkylsulphinyl, or alkylsulphonyl radicals, nitro, halogen, amino, hydroxyl, alkyl, alkoxy, pyridinyloxy, alkenyloxy, alkynyloxy, cyanoalkoxy, carboxyalkoxy, alkoxycarbonylalkoxy, dialkylamino, trifluoromethyl or cyano radicals, or $R_3$ is a naphthyl, tetrahydronaphthyl, biphenyl, methylenedioxyphenyl or ethylenedioxyphenyl radical, with the proviso that when n is 1 and $R_1$ and $R_2$ are hydrogen atoms, X cannot be an alkylene radical; and the tautomers, optically-active forms and physiologically acceptable salts thereof with inorganic and organic acids.

When the compounds of general formula (I) contain a centre of asymmetry or an asymmetric plane, the present invention also includes the optically-active forms and racemic mixtures of these compounds.

The compounds according to the present invention possess valuable pharmacological properties and, in particular, they have an inhibiting action on the erythrocyte aggregation and can thus be used for the treatment of diseases of the heart and circulatory system in the pathogenesis of which the aggregation of erythrocytes plays an important part, for example, peripheral, coronary and cerebral circulatory disturbances and shock states. Furthermore, the compounds also influence the thrombocyte function. In addition they can increase the power of the heart and lower the blood pressure.

Compounds with a structure similar to that of the compounds according to the present invention are known from the prior art:

a) In Federal Republic of Germany Patent Specification No. 32 04 892 (Otsuka, application date 12.2.82) are described compounds (carbostyril derivatives) in which A is a hydrogen atom or an alkyl, alkenyl, alkynyl or phenylalkyl radical, $R_1$ and $R_2$ are hydrogen atoms, n is 1, B is an alkyl radical, X is an alkylene radical and $R_3$ is a phenyl radical which can be substituted by alkoxy, halogen or alkylenedioxy. These compounds increase the myocardial contraction, the coronary blood flow and have a blood pressure-lowering action and are, therefore, used as cardiotonics.

b) In Japanese Patent Applications Nos. 12515/1978 and 118771/1976 are described compounds (carbostyril derivatives) in which A and B have the meanings given above under a), $R_1$ as well as $R_2$ are hydrogen atoms, X is a methylene radical and $R_3$ is a phenyl radical which, if desired, can be substituted. These compounds are only described as being intermediates for the preparation of pharmaceutical chemicals.

The compounds known from the prior art are, for the case in which n is 1, $R_1$ and $R_2$ are hydrogen atoms and X can then not be an alkylene radical, not included within the scope of the present invention.

If, in general formula (I), A or B is an alkyl radical, then this is to be understood to be a straight-chained or branched radical containing up to 6 carbon atoms. In this sense, there are especially to be understood methyl, ethyl, propyl, butyl, isopropyl, isobutyl and tert.-butyl radicals. If, in general formula (I), A or B is an alkenyl or alkynyl radical, then this is to be understood to be a straight-chained or branched radical containing 2 to 6 carbon atoms. In this sense, there are especially preferred allyl, propargyl, butenyl and isobutenyl radicals. If, in general formula (I), A or B is a cycloalkyl radical, then this is to be understood to be a ring containing 3 to 7 carbon atoms. In this sense, there are especially preferred the cyclopropyl, cyclobutyl, cyclopentyl and cyclohexyl radicals.

For the case in which $R_1$ is a hydrogen atom or an alkyl or alkenyl radical, $R_1$ and $R_2$ can be the same or different. $R_2$ can, furthermore, be a carbonyl group substituted by alkyl, alkoxy, amino or hydrazino. The alkyl and alkoxy moieties mentioned above in the case of $R_1$ and $R_2$ can be straight-chained or branched, saturated or unsaturated and contain 1 to 6 or 2 to 6 carbon atoms, respectively. Preferred, however, are hydrogen atoms and methyl, ethyl, allyl, acetyl, propionyl, methoxycarbonyl, ethoxycarbonyl and hydrazinocarbonyl radicals for $R_1$ and $R_2$.

When $R_1$ is a hydrogen atom, then $R_2$ is preferably a straight-chained or branched alkyl radical containing up to 6 carbon atoms or a carbonyl group substituted by alkyl, alkoxy, amino or hydrazino. Preferred in this sense are methyl, ethyl, isopropyl, isobutyl, pentyl, allyl, acetyl, propionyl, methoxycarbonyl, ethoxycarbonyl and hydrazinocarbonyl radicals.

$R_1$ and $R_2$, together with the carbon atom to which they are attached, can also form a cycloalkyl ring containing 3 to 8 carbon atoms and preferably a spirocyclopropyl, spirocyclobutyl, spirocyclopentyl or spirocyclohexyl radical.

If $R_1$ is a cycloalkyl radical, then this can contain 3 to 7 carbon atoms. This is preferably one of the groups mentioned in the case of the definition of A or B but more preferably a cyclopentyl or cyclohexyl radical.

If, in general formula (I), X is an alkylene radical, then this is to be understood to be a straightchained or branched radical containing up to 6 carbon atoms, the methylene, ethylene, propylene and butylene radicals being especially preferred.

If, in general formula (I), n is 0, then the compounds are substituted 2,3-dihydro-2-oxo-1H-indole-4-carboxamides, 2,3-dihydro-2-oxo-1H-indole-5-carboxamides, 2,3-dihydro-2-oxo-1H-indole-6-carboxamides or 2,3-dihydro-2-oxo-1H-indole-7-carboxamides. If n is 1, then the compounds are 1,2,3,4-tetrahydro-2-oxo-5-quinolinecarboxamides, 1,2,3,4-tetrahydro-2-oxo-6-quinolinecarboxamides, 1,2,3,4-tetrahydro-2-oxo-7-quinolinecarboxamides or 1,2,3,4-tetrahydro-2-oxo-8quinoline carboxamides.

The heterocyclic five- and six-membered rings containing 1 to 4 or 1 to 5 heteroatoms, respectively, in which the heteroatoms in the said five- and six-membered rings can be the same or different and can be nitrogen, oxygen or sulphur atoms and can possibly carry an oxygen atom on one or more nitrogen atoms, are preferably pyrrolyl, furanyl, thiophenyl, pyrazolyl, imidazolyl, thiazolyl, tetrazolyl, isothiazolyl, oxazolyl, isoxazolyl, triazolyl, thiadiazolyl, oxadiazolyl, pyrazinyl, N,N'-dioxypyrazinyl, pyrimidinyl, N,N'-dioxypyrimidinyl, pyridazinyl, oxazinyl, thiazinyl, triazinyl, tetrazinyl, pyridinyl or N-oxypyridinyl radicals.

If the aromatic heterocyclic five- or six-membered rings are condensed with a phenyl ring, then the indolyl, indazolyl, benzimidazolyl, quinolinyl, isoquinolinyl, cinnolinyl, phthalazinyl, quinazolinyl, quinoxalinyl, benzofuranyl, benzothiophenyl, benzoxazolyl, benzisooxazolyl, benzothiazolyl, benzoisothiazolyl, benzotriazolyl and benzothiadiazolyl radicals are preferred.

If the aromatic heterocyclic five- and six-membered rings are condensed with a further aromatic heterocyclic five- or six-membered ring to give a bicyclic radical, then these are preferably naphthyridinyl, pteridinyl, purinyl, indolizinyl, thiopheno[2,3-9- pyrazinyl, imidazo[1,2-a]pyridinyl or triazolo[4,3-a]pyridinyl radicals.

$R_3$ is especially preferably a pyridinyl, tetrazolyl, triazolyl, 1,2,4-triazolo[4,3-a]pyridinyl, methylenedioxyphenyl, ethylenedioxyphenyl, naphthyl, tetrahydronaphthyl, quinolinyl or biphenyl radical or a phenyl ring of general formula (II).

If the above-mentioned six-membered rings are substituted by a pyridinyloxy radical, then the 3-pyridinyloxy radical is preferred. If the above-mentioned six-membered ring is substituted by a phenyloxy radical, then there is especially preferred a linking with a pyridinyl radical as heterocyclic six-membered ring.

Alkyl, alkoxy and alkylthio substituents in the heterocyclic five- and six-membered rings, the bicyclic radicals and the pyridinyloxy and phenyloxy radicals can contain up to 6 and preferably up to 4 carbon atoms. The methyl, ethyl, methoxy, ethoxy, methylthio and ethylthio radicals are preferred. A halogen atom is to be understood to be a fluorine, chlorine or bromine atom and preferably a fluorine or chlorine atom.

If $R_3$ is a phenyl radical of general formula (II), then the alkyl moiety of the substituents mentioned in the case of $R_4$, $R_5$ and $R_6$ can contain up to 8 and preferably up to 5 carbon atoms. Preferred in this sense are, for example, the methanesulphonyloxy, ethanesulphonyloxy, n-propanesulphonyloxy, isopropanesulphonyloxy, trifluoromethanesulphonyloxy, methylsulphenylmethyl, ethylsulphenylmethyl, n-propylsulphenylmethyl, methylsulphinylmethyl, ethylsulphinylmethyl, methylsulphonylmethyl, ethylsulphonylmethyl, n-propylsulphonylmethyl, methylsulphonylamino, ethanesulphonylamino, n-propanesulphonylamino, trifluoromethanesulphonylamino, N-methyl-methanesulphonylamino, N-ethyl-methanesulphonylamino, N-methyl-ethanesulphonylamino, N-ethyl-ethanesulphonylamino, N-isopropyl-ethanesulphonylamino, N-methyl-n-propanesulphonylamino, N-n-propyl-n-propanesulphonylamino, N-methyl-trifluoromethanesulphonylamino, N-ethyl-trifluoromethanesulphonylamino, N-isopropyl-trifluoromethanesulphonylamino, methoxycarbonyl, ethoxycarbonyl, propoxycarbonyl, isopropoxycarbonyl, methylaminocarbonyl, ethylaminocarbonyl, dimethylaminocarbonyl, di-n-propylaminocarbonyl, N-methyl-ethylaminocarbonyl, trifluoromethyl, methylaminosulphonyl, ethylaminosulphonyl, n-propylaminosulphonyl, n-butylaminosulphonyl, n-pentylaminosulphonyl, dimethylaminosulphonyl, diethylaminosulphonyl, di-n-propylaminosulphonyl, N-methyl-isopropylaminosulphonyl, propionylamino, methylcarbonylamino, ethylaminocarbonylamino and propylaminocarbonylamino radicals, methyl, ethyl, propyl, butyl, pentyl, hexyl, heptyl, octyl, methoxy, ethoxy, propoxy, allyloxy, but-2-enyloxy, but-3-enyloxy, pent-2-enyloxy, propargyloxy, but-2-ynyloxy, but-3-ynyloxy, cyanomethoxy, cyanoethoxy, methoxycarbonylmethoxy, methoxycarbonylethoxy, methylthio, ethylthic, methylsulphinyl, ethylsulphinyl, methylsulphonyl and ethylsulphonyl radicals.

$R_4$ is especially preferably a hydrogen atom or a 1-imidazolyl, 2-imidazolyl, 6-oxo-(1H)-3-pyridazinyl, 4,5-dihydro-6-oxo-(1H)-3-pyridazinyl, 4,5-dihydro-4-methyl-6-oxo-(1H)-3-pyridazinyl radical, an alkylsulphonyloxy, trifluoromethylsulphonyloxy, alkylsulphenylmethyl, alkylsulphinylmethyl, alkylsulphonylmethyl, alkylsulphonylamino, N-alkyl-alkylsulphonylamino, trifluoromethylsulphonylamino or N-alkyl-trifluoromethylsulphonylamino radical, a carbonyl group substituted by hydroxyl, alkoxy, amino, alkylamino or dialkylamino or a sulphonyl group substituted by amino, dialkylamino or morpholino, in which each of the above-mentioned alkyl moieties can contain 1 or 2 carbon atoms, a nitro or cyano group or an alkylaminosulphonyl radical containing up to 4 carbon atoms, an alkylcarbonylamino, aminocarbonylamino or N-alkyl-aminocarbonylamino radical, an alkylthio, alkylsulphinyl or alkylsulphonyl radical, in which each of the above-mentioned alkyl moieties can contain 1 or 2 carbon atoms, a halogen atom, an amino or hydroxyl group, a dialkylamino, alkyl, alkoxy, alkenyloxy or alkynyloxy radical, preferably containing up to 3 carbon atoms, a 3-pyridinyloxy, cyanomethoxy, methoxycarbonylmethoxy or trifluoromethyl radical; $R_5$ is especially preferably a hydrogen atom, an alkyl radical containing up to 3 carbon atoms, an alkoxy or dialkylamino radical with 1 or 2 carbon atoms in each alkyl moiety, a halogen atom or an amino group; and $R_6$ is especially preferably a hydrogen atom or a methoxy radical.

The phenyl moiety can contain up to 3 of the said substituents.

Preferred monosubstituted phenyl compounds are the hydroxy-, $C_1$-$C_8$-alkyl-, $C_1$-$C_3$-alkoxy-, allyloxy-, propargyloxy-, cyanomethoxy-, methoxycarbonylmethoxy-, halo-, nitro-, cyano-, aminocarbonyl-, amino-, $C_1$-$C_3$-dialkylamino-, $C_1$-$C_3$-alkylthio-, $C_1$-$C_3$-alkylsulphinyl-, $C_1$-$C_3$-alkylsulphonyl-, $C_1$-$C_3$-alkylsulphonyloxy-, 3-pyridinyloxy- and 4,5-dihydro-6-oxo-(1H)-pyridazinyl-phenyls, the substituent being in the 2-, 3- or 4-position.

Preferred disubstituted phenyls contain, as substituents, alkanesulphonyloxy, trifluoromethylsulphonyloxy, alkylsulphenylmethyl, alkylsulphinylmethyl, alkylsulphonylmethyl, alkylsulphonylamino, N-alkyl-alkylsulphonylamino, trifluoromethylsulphonylamino or N-alkyl-trifluoromethylsulphonylamino radicals, carbonyl groups substituted by hydroxy, alkoxy, amino, alkylamino or dialkylamino or sulphonyl groups substituted by amino, dialkylamino or morpholino, alkylaminosulphonyl, alkylcarbonylamino, aminocarbonylamino or N-alkylaminocarbonylamino radicals, hydroxyl groups, alkyl, alkoxy, allyloxy, propargyloxy, cyanomethoxy or methoxycarbonylmethoxy radicals, halogen atoms, cyano, nitro or amino groups, dialkylamino, alkylthio, alkylsulphinyl or alkylsulphonyl radicals, in which the two substituents can be the same or different and can be in the 2,3-, 2,4-, 2,5-, 2,6-, 3,4-or 3,5-position but preferably in the 2,4-, 2,5- or 3,4-position and the above-mentioned alkyl radicals, alone or in combination with other radicals, can contain up to 3 carbon atoms.

The preferred trisubstituted phenyl radical is the 3,4,5-trimethoxyphenyl radical.

Especially preferred compounds of general formula (I) are those in which A and B, independently of one another, are hydrogen atoms or benzyl or $C_1$-$C_4$-alkyl radicals and especially methyl, ethyl, propyl, isopropyl or isobutyl radicals, or $C_2$-$C_4$-alkenyl radicals and especially allyl radicals; $R_1$ and $R_2$ are the same and are $C_1$-$C_4$-alkyl radicals, especially methyl radicals, or $R_1$ and $R_2$, together with the carbon atom to which they are attached, form a $C_5$-$C_6$-cycloalkyl ring and especially a cyclopentyl ring, X is a valency bond or a $C_1$-$C_4$-alkylene chain and especially an ethylene chain and $R_3$ is a pyrrolyl, furanyl, thiophenyl, pyrazolyl, imidazolyl, isothiazolyl, thiazolyl, oxazolyl, triazolyl, tetrazolyl, thiadiazolyl, isoxazolyl, oxadiazolyl, pyridinyl, N-oxypyridinyl, pyrazinyl, N,N'-dioxypyrazinyl, pyridimidinyl, N,N'-dioxypyrimidinyl, pyridazinyl, oxazinyl, thiazinyl, triazinyl, tetrazinyl, indolyl, benzimidazolyl, benzthiazolyl, indazolyl, quinolinyl, pyridinyloxypyridinyl or phenoxypyridinyl radical, as well as derivatives substituted by $C_1$-$C_4$-alkyl, especially methyl or ethyl, $C_1$-$C_4$alkoxy, especially methoxy or ethoxy, $C_2$-$C_4$-alkenyloxy, especially allyloxy or butenyloxy, methylenedioxy, $C_1$-$C_4$-alkylthio, especially methylthio, chlorine, amino or hydroxyl, or in which $R_3$ is a phenyl radical of general formula (II), wherein $R_4$ is a hydrogen atom, a methanesulphonyloxy, trifluoromethanesulphonyloxy, methanesulphonylamino, trifluoromethanesulphonylamino, methylthio, methylsulphinyl, methylsulphonyl, hydroxyl, methyl, methoxy, propargyloxy, trifluoromethyl, 1-imidazolyl or 3-pyridinyloxy radical, pyridazinyl, for example a 4,5-dihydro-6-oxo-(1H)-pyridazinyl or 4,5-dihydro-4-methyl-6-oxo-(1H)-pyridazinyl radical, an allyloxy or isobutenyloxy radical or an ethoxycarbonylmethoxy radical, a chlorine or fluorine atom, a cyano group or a dimethylamino or diethylamino radical, $R_5$ is a hydrogen or chlorine atom or a methyl, methoxy or dimethylamino radical and $R_6$ is a hydrogen atom or a methoxy radical or $R_3$ is a naphthyl, tetrahydronaphthyl, biphenyl, methylenedioxyphenyl or ethylenedioxyphenyl radical.

The attachment of the amido group with the bicyclic radical preferably takes place in such a manner that when n is 0 the compounds are substituted 2,3-dihydro-2-oxo-1H-indole-5-carboxamides or 2,3-dihydro-2-oxo-1H-indole-6-carboxamides and when n is 1 the compounds are 1,2,3,4-tetrahydro-2-oxo-6-quinolinecarboxamide or 1,2,3,4-tetrahydro-2-oxo-7-quinolinecarboxamides.

The compounds of general formula (I) can be prepared by known methods, the following processes being especially advantageous.

Compounds of general formula (I) can be prepared by acylating an amine of the general formula:

$$R_3—X—NH—B \qquad (III)$$

in which $R_3$, X and B have the above-given meanings, with a carboxylic acid of the general formula:

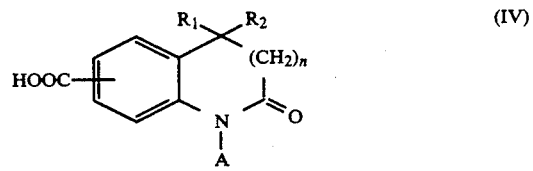

in which A, $R_1$, $R_2$ and n have the above-given meanings, or with a reactive derivative thereof. Amongst these reactive derivatives are to be understood esters, for example methyl and ethyl esters, anhydrides and acid halides, for example acid chlorides or bromides.

The preferred method for the reaction with the amines of general formula (III) consist in the reaction of approximately equimolar amounts of the amine and of the acid in the presence of an agent which removes water. For this purpose, there can be used, for example, polyphosphoric acid which then simultaneously serves as solvent. The reaction takes place at a temperature of from 50 to 200° C. In general, the end product of the general formula (I) precipitates out after the addition of water and, after filtration, is purified by recrystallisation or column chromatography.

Another preferred method for the preparation of the compounds of general formula (I) consists in the reaction of approximately equimolar amounts of the amine (III) and of the acid (IV) in an appropriate solvent with an approximately equivalent amount of a halogenation agent, for example phosphorus trichloride, phosphorus pentachloride or thionyl chloride, at a temperature of from ambient temperature to the reflux temperature of the reaction mixture. Appropriate solvents include methylene chloride, carbon tetrachloride, diethyl ether, toluene, xylene and chlorobenzene. In general, the product precipitates out of the solution and is recovered by filtration. If necessary, the reaction mixture can be concentrated until the product begins to precipitate out of the solution. As further condensation agents in the case of this reaction, there can be used acidic cation exchangers, sulphonium salts, sulphuric acid halides, 2-halopyridinium salts, phosphonium salts and N,N'-dicyclohexylcarbodiimide.

If, instead of the carboxylic acids, there are used the esters thereof, then working is carried out in the presence or absence of special solvents at a temperature in the range of from 20° C. to the boiling temperature of the reaction mixture. There is thereby preferred the reaction of approximately equimolar amounts of the amine and of the ester in polyphosphoric acid at a temperature of from 50 to 200° C. but it is also possible to work in an inert solvent, for example methylene chloride, benzene, toluene, or chlorobenzene, best in the presence of somewhat more than one equivalent of a base, for example sodium methanolate or butyl lithium or of sodium hydride in dimethyl sulphoxide.

If, instead of the carboxylic acids (IV), the anhydrides thereof are used, then the reaction with the amines of general formula (III) can even be carried out at somewhat lower temperatures. It is preferred to work in an inert solvent, for example dichloromethane, diethyl ether, benzene or toluene, at a temperature of from ambient temperature to 60° C. The amine and the anhydride are thereby mixed together in approximately equimolar amounts, whereby, in general, an exothermal reaction commences. After subsidence, the reaction mixture is gently warmed for some time for completion of the reaction.

If, instead of the carboxylic acids, there are used acid halides, then it is best preferred to work at a temperature of from −10° C. to ambient temperature. It is preferred to proceed in such a manner that, according to Schotten-Baumann, to an aqueous solution of the amine of general formula (III), which also contains a base, for example an alkali metal hydroxide, sodium carbonate or pyridine, there is slowly added dropwise, with ice cooling, the acid chloride and the reaction mixture is subsequently left to stand for some time at ambient temperature. This reaction is not only possible in water but also in an organic solvent, for example methylene chloride, diethyl ether, benzene or toluene. The amines can also be acylated practically quantitatively by carboxylic acid chlorides even without acidbinding agents by boiling the amine and the carboxylic acid chloride in an inert solvent, for example methylene chloride, benzene or toluene, until the ending of the gas evolution, which lasts about 1 to 24 hours. However, if an acid-binding agent, for example triethylamine or pyridine, is added in slight excess, then the reaction even takes place at a temperature of from −10° C. to ambient temperature.

The compounds of general formula (III) are known from the literature. Of the compounds of general formula (IV), the preparation of 2,3-dihydro-2-oxo-1H-indole-4-carboxylic acid has been described by J. von Braun and G. Hahn, Chem. Ber., 56. 2342/1923, the preparation of 2,3-dihydro-2-oxo-1H-indole-5-carboxylic acid in European Patent Specification No. 0,168,003 (Otsuka, application date 15.1.1986), the preparation of 1-ethyl-2,3-dihydro-2-oxo-(1H)-indole-5-carboxylic acid in European Patent Specification No. 0,181,136 (Pfizer, application date 14.5.86), the ion of 1',2'-dihydro-2'-oxo-spiro[cyclopropane-1,3'-(3H)-indole]-6'-carboxylic acid in Japanese Patent Specification No. 57/102863 (Takeda, application date 26.6.82), the preparation of 2,3-dihydro-2-oxo-(1H)-indole-7-carboxylic acid in U.S. Patent Specification No. 3,631,177 (SK&F, application date 28.12.1971), the preparation of 2,3-dihydro-3,3-dimethyl-2-oxo-1H-indole-5-carboxylic acid by R.F. Moore and S.G.P. Plant, J. Chem. Soc., 1951, 3475, the preparation of 2,3-dihydro-2-oxo-1H-indole-6-carboxylic acid by M. Fileti and E. Cairola, J. prakt. Chem., 46, 563/1892 and the preparation of 4-methyl-1,2,3,4-tetrahydro-2-oxo-6-quinolinecarboxamide in Japanese Patent Specification No. 63/112584 (Yoshitomi, application date 17.5.1988). The other compounds of general formula (IV) are new and also the subject of the present invention.

The process employed in the last-mentioned literature reference for the preparation of the specifically mentioned compounds can also be applied to the new compounds of general formula (IV). It consists in the reduction of compounds of the general formula:

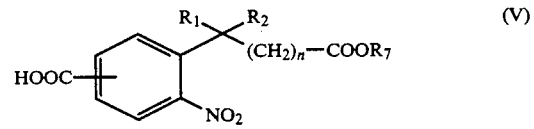

wherein $R_1$, $R_2$ and n have the above-given meanings and $R_7$ is a hydrogen atom or an alkyl radical and preferably a methyl or ethyl radical. The reduction takes place with ring closure so that the compounds of general formula (IV) are obtained directly. The reduction is preferably carried out in a solvent, for example water, methanol, ethanol, glacial acetic acid, ethyl acetate, dimethylformamide or a mixture of these solvents, with hydrogen in the presence of a catalyst, for example Raney nickel, platinum or palladium/charcoal, with metals, for example iron, tin, or zinc, in the presence of an acid, with salts, for example ferrous sulphate, stannous chloride, sodium sulphide, sodium hydrogen sulphite or sodium dithionite, or with hydrazine in the presence of Raney nickel at a temperature of from 0 to 100° C. but preferably at ambient temperature.

In the case of this reduction of the compounds of general formula (V), there are first formed compounds of general formula (IV), wherein A is a hydrogen atom, which can then, if desired, be alkylated to give compounds of general formula (IV), wherein A is an alkyl, alkenyl, alkynyl or cycloalkyl radical. These alkylations are preferably carried out in a solvent, for example acetone, methyl ethyl ketone, diethyl ether, benzene, toluene or dimethylformamide, at a temperature of from −30 to +100° C. and preferably of from 0 to 80° C. in the presence of a base, for example potassium hydroxide or sodium carbonate, and of an alkylation agent, for example an alkyl halide, alkenyl halide, alkynyl halide or cycloalkyl halide, or the corresponding sulphate.

The compounds of general formula (V) are prepared by nitrating compounds of the general formula:

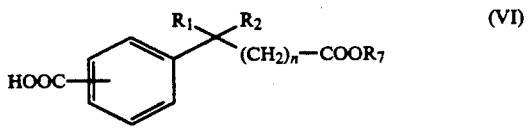
(VI)

$R_1$, $R_2$, $R_7$ and n have the above-given meanings. The nitration is preferably carried out with nitric acid in sulphuric acid at a temperature of from $-20°$ C. to $+50°$ C. However, it can also be carried out without sulphuric acid or, in place thereof, in water, glacial acetic acid or acetic anhydride, or with dinitrogen pentoxide in carbon tetrachloride in the presence of phosphorus pentoxide. As nitration reagents, there can also be used anhydrides, for example acetyl nitrate, or nitryl halides with ferric chloride, methyl nitrate and boron trifluoride or nitronium salts, for example $NO_2BF_4$, $NO_2PF_6$ or $NO_2CF_3SO_3$. For the nitration, there can also be used a mixture of nitric acid and nitrous acid which provides nitrogen tetroxide as the actual nitrating species.

A further process for the preparation of carboxylic acids of general formula (IV) consists in the saponification of nitriles of the general formula:

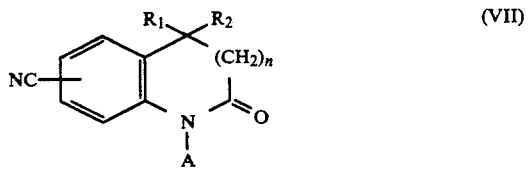
(VII)

wherein A, $R_1$, $R_2$ and n have the above-given meanings. The nitriles of general formula (VII) are obtained from amines of the general formula:

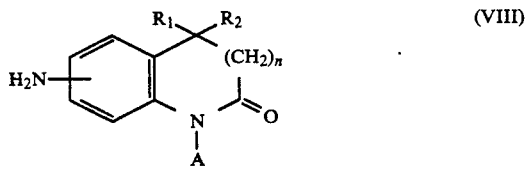
(VIII)

wherein A, $R_1$, $R_2$ and n have the above-given meanings, by diazotisation and reaction with a cyanide (Sandmeyer reaction). The compounds of general formula (VIII) are known from Federal Republic of Germany Patent Application No. 38 03 775.0 and from European Patent Application No. 89 101 868.1 (Boehringer Mannheim GmbH) and European Patent Specification No. 0,161,632.

Of the compounds of general formula (VII), the synthesis of 2,3-dihydro-2-oxo-(1H)-indole-5-carbonitrile has been described by G.P. Gassmann, D.P. Gilbert and T.-Y. Luth, J. Org. Chem., 42, 1340/1977. The other compounds of general formula (VII) are new and also the subject of the present invention.

The diazotisation of compounds of the general formula (VII) is preferably carried out under neutral or acidic conditions in solution or as suspension in a polar solvent, for example water, methanol, ethanol, glacial acetic acid, hydrochloric acid, sulphuric acid or phosphoric acid, at a temperature of from $-5$ to $+10°$ C.

For the diazotisation, there are preferably used inorganic salts or organic esters of nitrous acid, for example sodium or potassium nitrite or amyl nitrite. The solution of the diazonium salt thus obtained is added dropwise to an aqueous solution which contains cuprous cyanide and a cyanide salt, for example sodium or potassium cyanide, as well as a base, for example sodium or potassium carbonate or hydrogen carbonate. During the dropwise addition, the solution is kept at a temperature of from 20 to 100° C. and preferably of from 50 to 100° C.

Nitriles of general formula (VII), wherein A is a hydrogen atom (=general formula VIIa), can be alkylated to give nitriles of general formula (VII), wherein A is an alkyl, alkenyl, alkynyl or cycloalkyl radical (=general formula VIIb), wherein R' has the same meaning as R with the exception of a hydrogen atom).

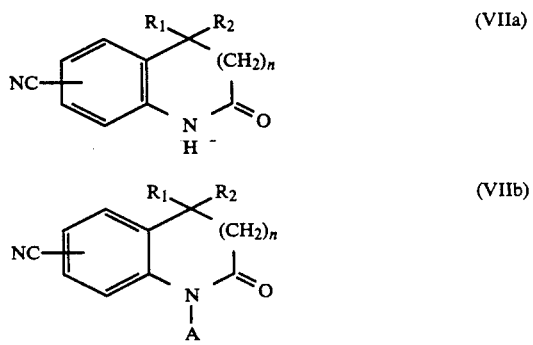

These alkylations are preferably carried out in a solvent. for example acetone, methyl ethyl ketone, diethyl ether. benzene, toluene or dimethylformamide. temperature of from $-30$ to $+100°$ C. and preferably of from 0 to 80° C. in the presence of a base with, for example, alkyl halides, alkenyl halides, alkynyl halides and cycloalkyl halides or the corresponding sulphates. Catalytic amounts of a crown ether can be added for the acceleration of the reaction.

The nitriles of general formula (VII) are now saponified to give the carboxylic acids of general formula (IV). The hydrolysis is advantageously carried out either in the presence of an acid, for example hydrochloric acid, sulphuric acid or trichloroacetic acid, or in the presence of a base, for example sodium hydroxide or potassium hydroxide, in an appropriate solvent, for example water or in mixtures, such as water/ethanol or water/dioxan, at a temperature of from 0 to 120° C. and preferably at the boiling point of the mixture.

Compounds of general formula (I) can also be converted into other compounds of general formula (I). This applies to the following:

a) The alkylation of compounds of general formula (I), wherein $R_3$ is a radical of general formula (II), one or more of the substituents $R_4$, $R_5$ and $R_6$ being hydroxyl or mercapto, to give the corresponding alkoxy or alkylthio compounds.

The reaction is preferably carried out in a solvent, for example acetone, diethyl ether, benzene, toluene or dimethylformamide, at a temperature of from $-30$ to $+100°$ C. and preferably at ambient temperature in the presence of a base, for example potassium hydroxide, and of an alkylation agent, for example an alkyl halide or alkyl sulphate.

b) The preparation of compounds of general formula (I), wherein $R_3$ is a radical of general formula (II) and $R_4$ is an alkylsulphinyl or alkylsulphonyl radical, by subsequent oxidation of a compound, wherein $R_4$ is an alkylthio radical. The oxidation is preferably carried out in a solvent or solvent mixture, for example water, water/pyridine, acetone, glacial acetic acid, dilute sulphuric acid or trifluoroacetic acid, depending upon the oxidation agent used, advantageously at a temperature of from $-80$ to $+100°$ C.

For the preparation of an alkylsulphinyl compound of general formula (I), the oxidation is advantageously carried out with one equivalent of the oxidation agent used, for example with hydrogen peroxide in glacial acetic acid, trifluoroacetic acid or formic acid at 0 to 20° C. or in acetone at 0 to 60° C., with a per acid, for example performic acid, in glacial acetic acid or trifluoroacetic acid at 0 to 50° C. or with m-chloroperbenzoic acid in methylene chloride or chloroform at $-20$ to 60° C., with sodium metaperiodate in aqueous methanol or ethanol at $-15$ to $+25°$ C., with bromine in glacial acetic acid or aqueous acetic acid, with N-bromosuccinimide in ethanol, with tert.-butyl hypochlorite in methanol at $-80$ to $-30°$ C., with iodobenzodichloride in aqueous pyridine at 0 to 50° C., with nitric acid in glacial acetic acid at 0 to 20° C., with chromic acid in glacial acetic acid or in acetone at 0 to 20° C. and with sulphuryl chloride in methylene chloride at $-70°$ C., the thioether-chlorine complex thereby obtained being advantageously hydrolysed with aqueous ethanol.

For the preparation of an alkylsulphonyl compound of general formula (I), the oxidation is advantageously carried out with two or more equivalents of the oxidation agent used, for example hydrogen peroxide in glacial acetic acid, trifluoroacetic acid or formic acid at 20 to 100° C. or in acetone at 0 to 60° C., with a per acid, for example performic acid or m-chloroperbenzoic acid, in glacial acetic acid, trifluoroacetic acid, methylene chloride or chloroform at a temperature of from 0 to 60° C., with nitric acid in glacial acetic acid at 0 to 20° C. or with chromic acid or potassium permanganate in glacial acetic acid, water/sulphuric acid or in acetone at 0 to 20° C.

c) The preparation of compounds of general formula (I), wherein $R_3$ is a radical of general formula (II) and $R_4$ is an alkanesulphonyloxy, trifluoromethanesulphonyloxy, alkanesulphonylamino or trifluoromethanesulphonylamino radical, by the subsequent reaction of a compound, wherein $R_4$ is a hydroxyl group, with a sulphonic acid of the general formula:

$$R_8—SO_3H \qquad (IX)$$

wherein $R_8$ is an alkyl radical or a trifluoromethyl radical, in the presence of an agent removing water and/or activating the acid or the amine, or with a reactive derivative thereof.

The reaction is advantageously carried out in a solvent or solvent mixture, for example methylene chloride, diethyl ether, tetrahydrofuran, dioxan or benzene, optionally in the presence of an acid-binding agent, for example sodium carbonate, triethylamine or pyridine, in which case the latter two can simultaneously also be used as solvent, in the presence of an agent activating the acid or removing water, for example thionyl chloride or phosphorus pentachloride, but preferably with a reactive derivative of a compound of general formula (VII), for example an anhydride or halide thereof, for example methanesulphonic acid chloride or ethanesulphonicacid chloride, at a temperature of from 0 to 100° C. and preferably at a temperature of from ambient temperature to 50° C.

d) The preparation of compounds of general formula (I), wherein $R_3$ is a radical of general formula (II) and $R_4$ is a carbonyl group substituted by amino, alkylamino or dialkylamino, by the subsequent reaction of a compound in which $R_4$ is a carboxyl group, or a reactive derivative thereof, for example an ester or acid chloride, with an amine of general formula:

$$R_9HNR_{10} \qquad (X)$$

wherein $R_9$ and $R_{10}$, which can be the same or different, are hydrogen atoms or alkyl radicals, or with a reactive derivative thereof if $R_4$ is a carboxyl group. The reaction is advantageously carried out in a solvent, for example methylene chloride, ethanol, chloroform, carbon tetrachloride, diethyl ether, tetrahydrofuran, dioxan, benzene, toluene, acetonitrile or dimethylformamide, optionally in the presence of an agent activating the acid or of a water-removing agent, for example in the presence of ethyl chloroformate, thionyl chloride, phosphorus trichloride, phosphorus pentoxide, N,N'-dicyclohexylcarbodiimide/N-hydroxysuccinimide, N,N'-carbonyldiimidazole or N,N'-thionyldiimidazole or triphenylphosphine/carbon tetrachloride, or of an agent activating the amino group, for example phosphorus trichloride, and optionally in the presence of an inorganic base, for example sodium carbonate, or of a tertiary organic base, for example triethylamine or pyridine, which can simultaneously serve as solvent, at a temperature of from $-25$ to $+250°$ C. but preferably at a temperature of from $-10°$ C. to the boiling temperature of the solvent used. Furthermore, during the reaction, water formed can be separated off by azeotropic distillation, for example by heating with toluene on a water separator, or by the addition of a drying agent, for example anhydrous magnesium sulphate or a molecular sieve.

However, the reaction is carried out especially advantageously with a corresponding halide, for example the carboxylic acid or sulphonic acid chloride, and an appropriate amine, in which case this can simultaneously serve as solvent, at a temperature of from 0 to 50° C.

e) The alkylation of compounds of the general formula:

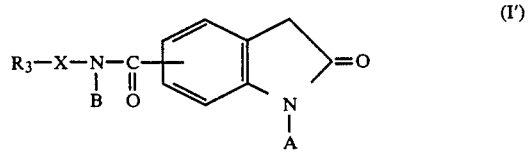

(I')

wherein A, B, $R_3$ and X have the above-given meanings, to give compounds of the general formula:

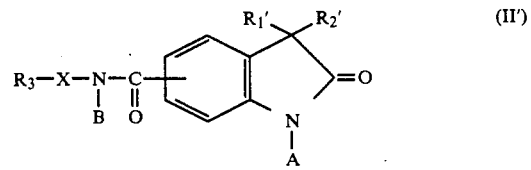

(II')

wherein A, B, R₃ and X have the above-given meanings and R₁' and R₂' are alkyl, alkenyl or cycloalkyl radicals or, together with the carbon atom to which they are attached, form a spirocyclic alkyl ring.

These reactions are preferably carried out in such a manner that the free NH positions in general formula (I') are protected, preferably by an acetyl radical, and then alkylated in a solvent, for example acetone, diethyl ether, benzene, toluene or dimethylformamide, at a temperature of from $-30$ to $+100°$ C. and preferably at ambient temperature in the presence of a base, for example potassium hydroxide, and of an alkylation agent of the general formula:

R₁'—Hal       (XI)

or of the general formula:

R₂'—Hal       (XII)

wherein R₁' and R₂' have the above-given meanings. The alkylation is preferably carried out in the presence of a phase transfer catalyst, for example N-benzyltriethylammonium bromide. The acetyl protective groups are subsequently removed. This already takes place in the case of working up after the alkylation but the deacetylation can be completed by briefly heating in an aqueous acid, for example hydrochloric acid or sulphuric acid.

f) The reaction of compounds of general formula (I), wherein R₂ is an alkoxycarbonyl radical, to give compounds of general formula (I), wherein R₂ is a hydrazinocarbonyl radical. For this purpose, the reaction is carried out in a solvent, for example ethanol, methanol or glacial acetic acid, with a slight excess of hydrazine hydrate at a temperature of from ambient temperature to the boiling point of the solvent.

g) The oxidation of compounds of general formula (I), wherein R₃ is a five- or six-membered ring with one or more nitrogen atoms, to give the corresponding N-oxides. The oxidation preferably takes place with one or more equivalents of an oxidising agent, for example hydrogen peroxide in glacial acetic acid, trifluoroacetic acid or formic acid, at 20 to 100° C. or in acetone at 0 to 60° C., with a per acid, for example performic acid or m-chloroperbenzoic acid, in glacial acetic acid, trifluoroacetic acid or methylene chloride, at a temperature of from 0 to 60° C.

h) The alkylation of compounds of the general formula I':

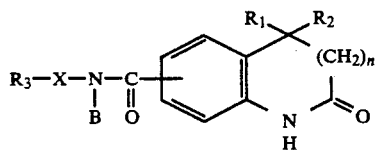

(I'')

wherein B, R₁, R₂, R₃, X and n have the above-given meanings, with alkylation agents of the general formula A'—Hal, wherein A' has the same meaning as A with the exception of hydrogen, to give compounds of the general formula:

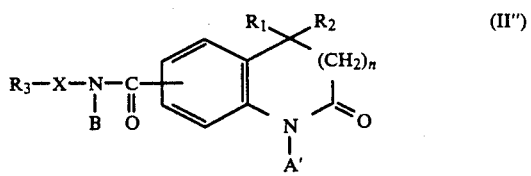

(II'')

wherein A', B, R₁, R₂, R₃, X and n have the above-given meanings. These alkylations are preferably carried out in a solvent, for example acetone, methyl ethyl ketone, diethyl ether, benzene, toluene or dimethylformamide, at a temperature of from $-30$ to $+100°$ C. and preferably of from 0 to 80° C. in the presence of a base, for example sodium hydroxide or potassium carbonate, and a small excess of the alkylation agent.

For the preparation of pharmaceutical compositions, the compounds of general formula (I) are mixed in known manner with appropriate pharmaceutical carrier materials, aroma, flavouring and colouring materials and formed, for example into tablets or dragees or, with the addition of appropriate adjuvants, suspended or dissolved in water or an oil, for example olive oil.

The compounds of general formula (I) and the salts thereof can be administered enterally or parenterally in liquid or solid form. As injection medium, it is preferred to use water which contains the additives usual in the case of injection solutions, for example stabilising agents, solubilising agents and/or buffers.

Such additives include, for example, tartrate and citrate buffers, ethanol, complex formers (such as ethylenediamine-tetraacetic acid and the non-toxic salts thereof) and high molecular weight polymers (such as liquid polyethylene oxide) for viscosity regulation. Solid carrier materials include, for example, starch, lactose, mannitol, methyl cellulose, talc, highly dispersed silicic acids, high molecular weight fatty acids (such as stearic acid), gelatine, agar-agar, calcium phosphate, magnesium stearate, animal and vegetable fats and solid high molecular weight polymers (such as polyethylene glycols). Compositions suitable for oral administration can, if desired, contain flavouring and sweetening agents.

The compounds are usually administered in amounts of from 10 to 1500 mg. per day, referred to a body weight of 75 kg. It is preferred to administer 1 to 2 tablets with a content of active material of 5 to 500 mg. 2 or 3 times a day. The tablets can also be retarded, in which case only 1 or 2 tablets with 20 to 700 mg. of active material have to be given once per day. The active material can also be administered by injection 1 to 8 times per day or by continuous infusion, in which case amounts of 10 to 1000 mg. per day normally suffice.

The carboxylic acids of general formula (IV) include, for example, the following compounds:

2,3-dihydro-3,3-diethyl-2-oxo-(1H)-indole-6-carboxylic acid 2,3-dihydro-3,3-dibutyl-2-oxo-(1H)-indole-6-carboxylic acid 2,3-dihydro-3-methyl-2-oxo-(1H)-indole-6-carboxylic acid 2,3-dihydro-3-ethyl-2-oxo-(1H)-indole-6-carboxylic acid 2,3-dihydro-3-propyl-2-oxo-(1H)-indole-6-carboxylic acid 2,3-dihydro-3-(1-methylethyl)-2-oxo-(1H)-indole-6-carboxylic acid
2,3-dihydro-3-ethoxycarbonyl-3-methyl-2-oxo-(1H)-indole-6-carboxylic acid
2,3-dihydro-3-hydrazinocarbonyl-3-methyl-2-oxo-(1H)-indole-6-carboxylic acid
2',3'-dihydro-2'-oxo-(1'H)-spiro[1,3'-cyclohexaneindole]-6'-carboxylic acid
1,2,3,4-tetrahydro-4,4-dimethyl-2-oxo-6-quinolinecarboxylic acid
2',3'-dihydro-2'-oxo-(1'H)-spiro[cyclopentane-1,3'indole]-5'-carboxylic acid.

The nitriles of general formula (VII) include, for example, the following compounds:
2,3-dihydro-3,3-diethyl-2-oxo-(1H)-indole-6-carbonitrile
2,3-dihydro-3,3-dibutyl-2-oxo-(1H)-indole-6-carbonitrile
2,3-dihydro-3-methyl-2-oxo-(1H)-indole-6-carbonitrile
2,3-dihydro-3-ethyl-2-oxo-(1H)-indole-6-carbonitrile
2,3-dihydro-3-propyl-2-oxo-(1H)-indole-6-carbonitrile
2,3-dihydro-3-(1-methylethyl)-2-oxo-(1H)-indole-6carbonitrile
2,3-dihydro-3-ethoxycarbonyl-3-methyl-2-oxo-(1H)-indole-6-carbonitrile
2,3-dihydro-3-hydrazinocarbonyl-3-methyl-2-oxo-(1H)-indole-6-carbonitrile
2',3'-dihydro-2'-oxo-(1'H)-spiro[1,3'-cyclopropaneindole]-6'-carbonitrile
2',3'-dihydro-2'-oxo-(1'H)-spiro[1,3'-cyclopentaneindole]-6'-carbonitrile
2',3'-dihydro-2'-oxo-(1'H)-spiro[1,3'-cyclohexaneindole]-6'-carbonitrile Apart from the compounds mentioned in the Examples, compounds of general formula (I) also include the following:
1. N-(4-diethylaminophenyl)-2,3-dihydro-3,3-dimethyl-2-oxo-(1H)-indole-6-carboxamide
2. N-(4-acetylphenyl)-2,3-dihydro-3,3-dimethyl-2-oxo-(1H)-indole-6-carboxamide
3. N-(4-ethylphenyl)-2,3-dihydro-3,3-dimethyl-2-oxo-(1H)-indole-6-carboxamide
4. N-(4-isopropylphenyl)-2,3-dihydro-3,3-dimethyl-2-oxo-(1H)-indole-6-carboxamide
5. N-(4-(1-methylpropyl)-phenyl)-2,3-dihydro-3,3-dimethyl-2-oxo-(1H)-indole-6-carboxamide
6. N-(4-bromophenyl)-2,3-dihydro-3,3-dimethyl-2-oxo-(1H)-indole-6-carboxamide
7. N-(3-hydroxyphenyl)-2,3-dihydro-3,3-dimethyl-2-oxo-(1H)-indole-6-carboxamide
8. N-(3-ethoxyphenyl)-2,3-dihydro-3,3-dimethyl-2-oxo-(1H)-indole-6-carboxamide
9. N-(3-acetylphenyl)-2,3-dihydro-3,3-dimethyl-2-oxo-(1H)-indole-6-carboxamide
10. N-(3-methylphenyl)-2,3-dihydro-3,3-dimethyl-2-oxo-(1H)-indole-6-carboxamide
11. N-(3-ethylphenyl)-2,3-dihydro-3,3-dimethyl-2-oxo-(1H)-indole-6-carboxamide
12. N-(3-hydroxymethylphenyl)-2,3-dihydro-3,3-dimethyl-2oxo-(1H)-indole-6-carboxamide
13. N-(3-fluorophenyl)-2,3-dihydro-3,3-dimethyl-2-oxo-(1H)-indole-6-carboxamide
14. N-(3-bromophenyl)-2,3-dihydro-3,3-dimethyl-2-oxo-(1H)-indole-6-carboxamide
15. N-(2-aminophenyl)-2,3-dihydro-3,3-dimethyl-2-oxo-(1H)-indole-6-carboxamide
16. N-(2-acetamidophenyl)-2,3-dihydro-3,3-dimethyl-2-oxo-(1H)-indole-6-carboxamide
17. N-(2-hydroxyphenyl)-2,3-dihydro-3,3-dimethyl-2-oxo-(1H)-indole-6-carboxamide
18. N-(2-ethoxyphenyl)-2,3-dihydro-3,3-dimethyl-2-oxo-(1H)-indole-6-carboxamide
19. N-(2-acetylphenyl)-2,3-dihydro-3,3-dimethyl-2-oxo-(1H)-indole-6-carboxamide
20. N-(2-methoxycarbonylphenyl)-2,3-dihydro-3,3-dimethyl-2-oxo-(1H)-indole-6-carboxamide
21. N-(2-ethoxycarbonylphenyl)-2,3-dihydro-3,3-dimethyl-2-oxo-(1H)-indole-6-carboxamide
22. N-(2-trifluoromethylphenyl)-2,3-dihydro-3,3-dimethyl-2-oxo-(1H)-indole-6-carboxamide
23. N-(2-ethylphenyl)-2,3-dihydro-3,3-dimethyl-2-oxo-(1H)-indole-6-carboxamide
24. N-(2-hydroxymethylphenyl)-2,3-dihydro-3,3-dimethyl-2-oxo-(1H)-indole-6-carboxamide
25. N-(2-(1-methylpropyl)-phenyl)-2,3-dihydro-3,3-dimethyl-2-oxo-(1H)-indole-6-carboxamide
26. N-(2-fluorophenyl)-2,3-dihydro-3,3-dimethyl-2-oxo-(1H)-indole-6-carboxamide
27. N-(2-bromophenyl)-2,3-dihydro-3,3-dimethyl-2-oxo-(1H)-indole-6-carboxamide
28. N-(2-cyanophenyl-2,3-dihydro-3,3-dimethyl-2-oxo-(1H)-indole-6-carboxamide
29. N-(4-(3-pyridinyloxy)-phenyl)-2,3-dihydro-3,3-dimethyl-2-oxo-(1H)-indole-6-carboxamide
30. N-(2-amino-4-chlorophenyl)-2,3-dihydro-3,3-dimethyl-2-oxo-(1H)-indole-6-carboxamide
31. N-(2-amino-4-methoxyphenyl)-2,3-dihydro-3,3-dimethyl-2-oxo-(1H)-indole-6-carboxamide
32. N-(2-amino-6-methylphenyl)-2,3-dihydro-3,3-dimethyl-2-oxo-(1H)-indole-6-carboxamide
33. N-(2-amino-5-chlorophenyl)-2,3-dihydro-3,3-dimethyl-2-oxo-(1H)-indole-6-carboxamide
34. N-(2-methyl-5-aminophenyl)-2,3-dihydro-3,3-dimethyl-2-oxo-(1H)-indole-6-carboxamide
35. N-(2-methyl-3-aminophenyl)-2,3-dihydro-3,3-dimethyl-2-oxo-(1H)-indole-6-carboxamide
36. N-(2-methoxy-5-aminophenyl)-2,3-dihydro-3,3-dimethyl-2-oxo-(1H)-indole-6-carboxamide
37. N-(2-amino-4-fluorophenyl)-2,3-dihydro-3,3-dimethyl-2-oxo-(1H)-indole-6-carboxamide
38. N-(2-methyl-4-aminophenyl)-2,3-dihydro-3,3-dimethyl-2-oxo-(1H)-indole-6-carboxamide
39. N-(2-methoxy-4-aminophenyl)-2,3-dihydro-3,3-dimethyl-2-oxo-(1H)-indole-6-carboxamide
40. N-(2-chloro-4-aminophenyl)-2,3-dihydro-3,3-dimethyl-2-oxo-(1H)-indole-6-carboxamide
41. N-(2-bromo-4-aminophenyl)-2,3-dihydro-3,3-dimethyl-2-oxo-(1H)-indole-6-carboxamide
42. N-(2,4-diaminophenyl)-2,3-dihydro-3,3-dimethyl-2-oxo-(1H)-indole-6-carboxamide
43. N-(2,6-dichloro-4-aminopheny-2,3-dihydro-3,3-dimethyl-2-oxo-(1H)-indole-6-carboxamide
44. N-(2-hydroxy-5-chlorophenyl)-2,3-dihydro-3,3-dimethyl-2-oxo-(1H)-indole-6-carboxamide
45. N-(2-hydroxy-5-methylphenyl)-2,3-dihydro-3,3-dimethyl-2-oxo-(1H)-indole-6-carboxamide
46. N-(2-thenyl)-2,3-dihydro-3,3-dimethyl-2-oxo-(1H)-indole-6-carboxamide
47. N-(2-thiazolyl)-2,3-dihydro-3,3-dimethyl-2-oxo-(1H)-indole-6-carboxamide
48. N-(5-methyl-3-isoxazolyl)-2,3-dihydro-3,3-dimethyl-2-oxo-(1H)-indole-6-carboxamide
49. N-(1,3,4-thiadiazol-2-yl)-2,3-dihydro-3,3-dimethyl-2-oxo-(1H)-indole-6-carboxamide
50. N-(5-methyl-1,3,4-thiadiazol-2-yl)-2,3-dihydro-3,3-dimethyl-2-oxo-(1H)-indole-6-carboxamide 51. N-(N-oxy-4-pyridinyl)-2,3-dihydro-3,3-dimethyl-2-oxo-(1H)-indole-6-carboxamide
52. N-(2-pyrazinyl)-2,3-dihydro-3,3-dimethyl-2-oxo-(1H)-indole-6-carboxamide
53. N-(2-pyrimidinyl)-2,3-dihydro-3,3-dimethyl-2-oxo-(1H)-indole-6-carboxamide
54. N-(1,2,4-triazin-3-yl)-2,3-dihydro-3,3-dimethyl-2-oxo-(1H)-indole-6-carboxamide
55. N-(6-methoxy-3-pyridinyl)-2,3-dihydro-3,3-dimethyl-2-oxo-(1H)-indole-6-carboxamide
56. N-(6-propoxy-3-pyridinyl)-2,3-dihydro-3,3-dimethyl-2-oxo-(1H)-indole-6-carboxamide
57. N-(6-isopropoxy-3-pyridinyl)-2,3-dihydro-3,3-dimethyl-2-oxo-(1H)-indole-6-carboxamide
58. N-(6-allyloxy-3-pyridinyl)-2,3-dihydro-3,3-dimethyl-2-oxo-(1H)-indole-6-carboxamide
59. N-(6-(4-pyridinyloxy)-3-pyridinyl)-2,3-dihydro-3,3-dimethyl-2-oxo-(1H)-indole-6-carboxamide
60. N-(6-phenoxy-3-pyridinyl)-2,3-dihydro-3,3-dimethyl-2-oxo-(1H)-indole-6-carboxamide
61. N-(6-(4-methoxyphenoxyl)-2,3-dihydro-3,3-dimethyl-2-oxo-(1H)-indole-6-carboxamide
62. N-(6-(3-trifluoromethylphenoxy)-3-pyridinyl)-2,3-dihydro-3,3-dimethyl-2-oxo-(1H-indole-6-carboxamide
63. N-(6-(4-cyanophenoxy)-3-pyridinyl)-2,3-dihydro-3,3-dimethyl-2-oxo-(1H)-indole-6-carboxamide
64. N-(6-(2-methoxyphenoxy)-3-pyridinyl)-2,3-dihydro3,3-dimethyl-2-oxo-(1H)-indole-6-carboxamide
65. N-(6-(3-methoxyphenoxy)-3-pyridinyl)-2,3-dihydro-3,3-dimethyl-2-oxo-(1H)-indole-6-carboxamide
66. N-(6-(4-methylphenoxy)-3-pyridinyl)-2,3-dihydro-3,3-dimethyl-2-oxo-(1H)-indole-6-carboxamide
67. N-(6-(4-ethoxycarbonylphenoxy)-3-pyridinyl)-2,3-dihydro-3,3-dimethyl-2-oxo-(1H)-indole-6carboxamide
68. N-(2-benzimidazolyl)-2,3-dihydro-3,3-dimethyl-2-oxo-(1H)-indole-6-carboxamide
69. N-(2-benzthiazolyl)-2,3-dihydro-3,3-dimethyl-2-oxo-(1H)-indole-6-carboxamide
70. N-(2-methyl-4-quinolinyl)-2,3-dihydro-3,3-dimethyl-2-oxo-(1H)-indole-6-carboxamide
71. N-(5-methyl-7-hydroxy-[1,8]-naphthyridin-2-yl)-2,3-dihydro-3,3-dimethyl-2-oxo-(1H)-indole-6-carboxamide
72. N-(1,4-dihydroxy-5-phthalazinyl)-2,3-dihydro-3,3-dimethyl-2-oxo-(1-indole-6-carboxamide
73. N-phenyl-2',3'-dihydro-2'-oxo-(1'H)-spiro[1,3cyclopropaneindole]-6'-carboxamide
74. N-phenyl-2',3'-dihydro-2'-oxo-(1'H)-spiro[1,3'-cyclohexaneindole]-6'-carboxamide
75. 2,3-dihydro-3,3-dimethyl-N-benzyl-N-phenyl-2-oxo-(1H)-indole-6-carboxamide
76. 2,3-dihydro-3,3-dimethyl-1-ethyl-N-ethyl-N-(4-fluorophenyl)-2-oxo-(1H)-indole-6-carboxamide
77. N-(4-biphenyl)-2,3-dihydro-3,3-dimethyl-2-oxo-(1H)-indole-6-carboxamide; m.p. 288-291° C.
78. N-(4-methylsulphonylaminophenyl)-2,3-dihydro-3,3-dimethyl-2-oxo-(1H)-indole-6-carboxamide
79. N-(4-phenylsulphonylaminophenyl)-2,3-dihydro-3,3-dimethyl-2-oxo-(1H)-indole-6-carboxamide.

The following Examples are given for the purpose of illustrating the present invention:

EXAMPLE 1

2,3-Dihydro-3,3-dimethyl-N-phenyl-2-oxo-(1H)-indole-6-carboxamide a) 25 g. (0.142 mol) 6-Amino-1,3-dihydro-3,3-dimethyl-(2H)-indolin-2-one in 250 ml. 2N hydrochloric acid were mixed, while cooling with ice, within the course of 15 minutes with a solution of 10.3 g. (0.15 mol) sodium nitrite in 20 ml. water and, after the addition, stirred for 15 minutes. After mixing with 2.13 g. (0.036 mol) urea, the clear solution, after stirring for a further 10 minutes, was added dropwise to a solution, warmed to 50° C., of 24.4 g. (0.5 mol) sodium cyanide, 15.2 g. (0.17 mol) cuprous cyanide and 22.6 g. (0.21 mol) sodium carbonate in 820 ml. water and heated for 5 minutes to 90° C. After cooling, the precipitate was filtered off with suction, washed with water and, after drying, recrystallised from ethanol. There were obtained 15 g. (57% of theory) 2,3-dihydro-3,3-dimethyl-2-oxo-(1H)-indole-6-carbonitrile in the form of colourless crystals; m.p. 243-246° C.

b) 12.2 g. 2,3-Dihydro-3,3-dimethyl-2-oxo-(1H)-indole-6-carbonitrile were heated under reflux to the boil in 150 ml. 20% aqueous potassium hydroxide solution, cooled, neutralised with concentrated hydrochloric acid and the crystals filtered off with suction and washed with water. There were obtained 13.1 g. (98% of theory) 2,3-dihydro-3,3-dimethyl-2-oxo-(1H-indole-6-carboxylic acid; m.p. 295-300° C. (decomp.).

c) 8 g. 2,3-Dihydro-3,3-dimethyl-2-oxo-(1H)-indole-6-carboxylic acid and 1 drop of dimethylformamide were heated in 50 ml. thionyl chloride for 1 hour to the boil under reflux, the substance thereby going into solution. The thionyl chloride was removed under vacuum, the residue was suspended in dichloromethane and a solution of 1.6 ml. aniline and 2.7 ml. triethylamine in 30 ml. dichloromethane added dropwise thereto at an internal temperature of 15° C. The reaction mixture was stirred for 15 minutes at ambient temperature, the solvent was removed in a vacuum and the residue was digested with water, filtered off with suction and recrystallised from ethyl acetate. There were obtained 2.8 g. (56% of theory) of the title compound; m.p. 205-206° C.

By reaction with the given amines instead of aniline, the following compounds were obtained analogously to Example 1:

| | designation | yield m.p. | recryst. from |
|---|---|---|---|
| 2 | 2,3-dihydro-3,3-dimethyl-N-(3-trifluoromethylphenyl)-2-oxo-indole-6-carboxamide from 3-trifluoromethylaniline | 34% 182-186° C. | ethyl acetate |
| 3 | 2,3-dihydro-3,3-dimethyl-N-(4-pyridinyl)-2-oxo-(1H)-indole-6-carboxamide from 4-pyridineamine | 53% 336-341° C. | methanol |
| 4 | 2,3-dihydro-3,3-dimethyl-N-[6-(3-pyridinyloxy)-3-pyridinyl]-2-oxo-(1H)-indole-6-carboxamide from 2-(3-pyridinyloxy)-5-pyridinamine | 48% 198-200° C. | ethyl acetate |
| 5 | 2,3-dihydro-3,3-dimethyl-N-[4-(4,5-dihydro-4-methyl-6-oxo-(1H)-3-pyridazinyl)-phenyl]-2-oxo-(1H)-indole-6-carboxamide from 4-(4,5- | 78% 273-278° C. | isopropanol |

-continued

| designation | yield m.p. | recryst. from |
|---|---|---|
| dihydro-4-methyl-6-oxo-(1H)-3-pyridazinyl)-aniline | | |
| 6 2,3-dihydro-3,3-dimethyl-N-(4-nitrophenyl)-2-oxo-(1H)-indole-6-carboxamide from 4-nitroaniline | 62% 268–271° C. | ethanol |
| 7 2,3-dihydro-3,3-dimethyl-N-(4-dimethylaminophenyl)-2-oxo-(1H)-indole-6-carboxamide × 0.5 $H_2O$ from 4-dimethylaminoaniline | 60% 333–335° C. | DMF/water |
| 8 2,3-dihydro-3,3-dimethyl-N-(4-hydroxy-2-methylphenyl)-2-oxo-(1H)-indole-6-carboxamide × $H_2O$ from 4-hydroxy-2-methylaniline | 17% 110–130° C. | ethyl acetate |
| 9 2,3-dihydro-3,3-dimethyl-N-(2-(2-pyridinyl)-ethyl)-2-oxo-(1H)-indole-6-carboxamide from 2-(2-pyridinyl)-ethaneamine | 70% 185–187° C. | ethyl acetate |
| 10 2,3-dihydro-3,3-dimethyl-N-(3-(1,2,4-triazolo[4,3-a]-pyridinyl))-2-oxo-(1H)-indole-6-carboxamide × 0.5 $H_2O$ from 1,2,4-triazolo-[4,3-a]pyridine-3-amine | 42% 310–312° C. | methanol |
| 11 2,3-dihydro-3,3-dimethyl-N-(4-methylphenyl)-2-oxo-(1H)-indole-6-carboxamide from 4-methylaniline | 48% 245–247° C. | ethanol |
| 12 2,3-dihydro-3,3-dimethyl-N-(4-fluorophenyl)-2-oxo-(1H)-indole-6-carboxamide from 4-fluoroaniline | 64% 235–236° C. | ethanol |
| 13 2,3-dihydro-3,3-dimethyl-N-(4-cyanophenyl)-2-oxo-(1H)-indole-6-carboxamide from 4-cyanoaniline | 44% 264–266° C. | ethyl acetate |
| 14 2,3-dihydro-3,3-dimethyl-N-(3-methoxyphenyl)-2-oxo-(1H)-indole-6-carboxamide from methoxyaniline | 68% 211–213° C. | ethyl acetate |
| 15 2,3-dihydro-3,3-dimethyl-N-(3-chlorophenyl)-2-oxo-(1H)-indole-6-carboxamide from 3-chloroaniline | 46% 233–235° C. | ethyl acetate |
| 16 2,3-dihydro-3,3-dimethyl-N-(2-methylphenyl)-2-oxo-(1H)-indole-6-carboxamide from 2-methylaniline | 45% 219–221° C. | ethyl acetate |
| 17 2,3-dihydro-3,3-dimethyl-N-(4-hydroxyphenyl)-2-oxo-(1H)-indole-6-carboxamide from 4-hydroxyaniline | 58% 218–221° C. | ethyl acetate |
| 18 2,3-dihydro-3,3-dimethyl-N-(4-methoxyphenyl)-2-oxo-(1H)-indole-6-carboxamide from 4-methoxyaniline | 62% 241–242° C. | ethanol/water |
| 19 2,3-dihydro-3,3-dimethyl-N-(4-ethoxyphenyl)-2-oxo-(1H)-indole-6-carboxamide from 4-ethoxyaniline | | |
| 20 2,3-dihydro-3,3-dimethyl-N-(4-allyloxyphenyl)-2-oxo-(1H)-indole-6-carboxamide from allyloxyaniline | | |
| 21 2,3-dihydro-3,3-dimethyl-N-(3,4-methylenedioxyphenyl)-2-oxo-(1H)-indole-6-carboxamide from 3,4-methylenedioxyaniline | 34% 266–271° C. | ethanol |
| 22 2,3-dihydro-3,3-dimethyl-N-(3,4-ethylenedioxyphenyl)-2-oxo-(1H)-indole-6-carboxamide from 3,4-ethylenedioxyaniline | 25% 275–278° C. | ethanol |
| 23 2,3-dihydro-3,3-dimethyl-N-(4-(5,6,7,8-tetrahydronaphthyl))-2-oxo-(1H)-indole-6-carboxamide from 2-(5,6,7,8-tetrahydronaphthyl)-amine | | |
| 24 2,3-dihydro-3,3-dimethyl-N-(5-(1H)-tetrazolyl)-2-oxo-(1H)-indole-6-carboxamide from 5-(1H)-tetrazolylamine | | |
| 25 2,3-dihydro-3,3-dimethyl-N-(3-(1H)-(1,2,4-triazolyl))-2-oxo-(1H)-indole-6-carboxamide from 3-(1H)-(1,2,4-triazolyl)-amine | | |
| 26 2,3-dihydro-3,3-dimethyl-N-(2-hydroxy-4-methylphenyl)-2-oxo-(1H)-indole-6-carboxamide from 2-hydroxy-4-methylaniline | | |
| 27 2,3-dihydro-3,3-dimethyl-N-(3-cyanophenyl)-2-oxo-(1H)-indole-6-carboxamide from 3-cyanoaniline | 67% 304–307° C. | ethanol/ethyl acetate |
| 28 2,3-dihydro-3,3-dimethyl-N-(4-ethoxycarbonylmethyloxyphenyl)-2-oxo-(1H)-indole-6-carboxamide from 4-(ethoxycarbonylmethyloxy)-aniline | 44% 204–206° C. | ethyl acetate |

EXAMPLE 29

2,3-Dihydro-3,3-dimethyl-N-(4-aminophenyl)-2-oxo-(1H)-indole-6-carboxamide 2.6 g. (8 mmol) 2,3-Dihydro-3,3-dimethyl-N-(4-nitrophenyl)-2-oxo-(1H)-indole-6-carboxamide (from Example 6) in 50 ml. methanol were hydrogenated in the presence of 0.3 g. 10% palladium on charcoal at normal pressure and ambient temperature. After 2 hours, the reaction mixture was filtered with suction, the solvent was removed from the filtrate in a vacuum and the residue purified by column chromatography (silica gel; elution agent dichloromethane/methanol saturated with ammonia 95:5 v/v). The solvent was removed in a vacuum, the residue was digested with ethyl acetate, filtered off with suction and the residue dried in a vacuum at 100° C. There was obtained 1.4 g. (61% of theory) of the title compound; m.p. 216–218° C. The title compound contained adhering thereto 0.5 mole of water per mole.

EXAMPLE 30

2,3-Dihydro-3,3-dimethyl-N-(4-methoxyphenyl)-2-oxo-(1H)-indole-5-carboxamide 2.3 g. (10 mmole) 2,3-dihydro-3,3-dimethyl-2-oxo-(1H)-indole-5-carboxylic acid, 1 drop of dimethylformamide and 15 ml. thionyl chloride were heated to the boil under reflux for 30 minutes. The thionyl chloride was removed under a vacuum and the crude product was used without further purification. The crude product was dissolved in 20 ml. dichloromethane and added dropwise to a solution of 2.5 g. (20 mmol) p-anisidine in 50 ml. dichloromethane while cooling with ice. After 15 minutes, 50 ml. water were added thereto, the organic phase was separated off and the solvent removed under vacuum. The residue was purified by column chromatography (400 ml. silica gel 60, dichloromethane/methanol 20:1 v/v). The pure fractions were evaporated under vacuum, the residue was digested with diethyl ether, filtered off with suction and dried in a vacuum at 100° C. There was obtained 1.9 g. (61% of theory) of the title compound; m.p. 169–171° C.

By the reaction of 2,3-dihydro-3,3-dimethyl-2-oxo-(1H)-indole-5-carboxylic acid with the mentioned aniline derivatives, the following compounds were obtained analogously to Example 30:

| designation | yield m.p. | recryst. from |
| --- | --- | --- |
| 31 2,3-dihydro-3,3-dimethyl-N-(4-cyanophenyl)-2-oxo-(1H)-indole-5-carboxamide from 4-cyanoaniline | | |
| 32 2,3-dihydro-3,3-dimethyl-N-(3-trifluoromethylphenyl)-2-oxo-(1H)-indole-5-carboxamide from 4-trifluoromethylaniline | | |
| 33 2,3-dihydro-3,3-dimethyl-N-(4-ethoxycarbonylmethyloxyphenyl)-2-oxo-(1H)-indole-5-carboxamide from 4-(ethoxycarbonylmethyloxy)-aniline | 50% 127–129° C. | ethyl acetate |

EXAMPLE 34

2,3-Dihydro-3,3-dimethyl-1-ethyl-N-phenyl-2-oxo-(1H)-indole-6-carboxamide a) 3.1 ml. (0.038 mol) Ethyl iodide were added dropwise at ambient temperature to 5.9 g. (0.032 mol) 2,3-dihydro-3,3-dimethyl-2-oxo-(1H)-indole-6-carbonitrile (from Example 1a) and 5.3 g. (0.38 mol) potassium carbonate in 50 ml. dimethylformamide. The reaction mixture was further stirred for 2 hours at 40° C., then poured into 220 ml. water and the precipitate filtered off with suction. There were obtained 6.7 g. (100% of theory) 2,3-dihydro-3,3-dimethyl-1-ethyl-2-oxo-(1H)-indole-6-carbonitrile; m.p. 81–83° C.

b) According to the procedure of Example 1a, there were obtained therefrom 7.3 g. (98% of theory) 2,3-dihydro-3,3-dimethyl-1-ethyl-2-oxo-(1H)-indole-6-carboxylic acid; m.p. 228–231° C.

c) According to the procedure of Example 1c, from 3.8 g. (0.015 mol) of this compound there were obtained 3.6 g. (78% of theory) of the title compound; m.p. 227–230° C.

EXAMPLE 35

2,3-Dihydro-3,3-dimethyl-1-ethyl-N-(4-fluorophenyl)-2-oxo-(1H)-indole-6-carboxamide By reaction of the 2,3-dihydro-3,3-dimethyl-1-ethyl-2-oxo-(1H)-indole-6-carboxylic acid prepared in Example 34b with 4-fluoroaniline analogously to Example 1c, there was obtained the title compound in a yield of 58% of theory; m.p. 179–181° C., after recrystallisation from ethyl acetate.

EXAMPLE 36

2,3-Dihydro-3,3-dimethyl-1-ethyl-N-(4-cyanophenyl)-2-oxo-(1H)-indole-6-carboxamide Analogously to Example 35, by reaction with 4-cyanoaniline, there was obtained the title compound in a yield of 63% of theory; m.p. 211–213° C., after recrystallisation from ethyl acetate.

EXAMPLE 37

2,3-Dihydro-1,3,3-trimethyl-N-phenyl-2-oxo-(1H)-indole-6-carboxamide 2.8 g. (10 mmol) 2,3-Dihydro-3,3-dimethyl-N-phenyl-2-oxo-(1H)-indole-6-carboxamide, 2.8 g. (20 mmol) methyl iodide and 2.5 g. (20 mmol) potassium carbonate were stirred in 50 ml. dimethylformamide for 3 hours at 70° C. After cooling, the reaction mixture was mixed with water, decanted and again mixed with water. The residue was purified by column chromatography (RP-18, methanol:water:ammonium hydroxide 80:20:1 v/v/v). Pure fractions were evaporated until the commencement of crystallisation, subsequently filtered off with suction and washed with water. There were obtained 2.3 g. (78% of theory) of the title compound; m.p. 184–186° C.

EXAMPLE 38

2,3-Dihydro-3,3-dimethyl-1-propyl-N-phenyl-2-oxo-(1H)-indole-6-carboxamide was obtained in a yield of 65% of theory analogously to Example 37 by reaction with propyl iodide; m.p. 160–162° C.

EXAMPLE 39

2,3-Dihydro-3,3-dimethyl-1-allyl-N-phenyl-2-oxo-(1H)-indole-6-carboxamide was obtained in a yield of 63% of theory analogously to Example 37 by reaction with allyl bromide; m.p. 186–188° C.

EXAMPLE 40

2,3-Dihydro-3,3-dimethyl-1-(2-methylpropyl)-N-phenyl-2-oxo-(1H)-indole-6-carboxamide was obtained in a yield of 53% of theory analogously to Example 37 by reaction with isobutyl iodide; m.p. 143–144° C.

EXAMPLE 41

2,3-Dihydro-3,3-dimethyl-N-ethyl-N-phenyl-2-oxo-(1H)-indole-6-carboxamide was obtained in a yield of 48% of theory analogously to Example 1c by reaction with N-ethylaniline; m.p. 221–223° C.

EXAMPLE 42

4,4-Dimethyl-1,2,3,4-tetrahydro-N-phenyl-2-oxo-7-quinolinecarboxamide a) According to the procedure of Example 1a, from 3,4-dihydro-(1H)-quinolin-2-one there were obtained 4.0 g. (63% of theory) 4,4-dimethyl-1,2,3,4-tetrahydro-2-oxo-7-quinolinecarbonitrile; m.p. 207–209° C.

b) According to the procedure of Example 1b, there was obtained therefrom a quantitative yield of 4,4-dimethyl-1,2,3,4-tetrahydro-2-oxo-7-quinolinecarboxylic acid; m.p. 314–316° C.

c) 2.7 g. (12.3 mmol) 4,4-Dimethyl-1,2,3,4-tetrahydro-2-oxo-7-quinolinecarboxylic acid were added to a solution of 3.8 g. (18.5 mmol) N,N'-dicyclohexylcarbodiimide and 1.1 ml. (12.3 mmol) aniline in 80 ml. dichloromethane. The reaction mixture was stirred for 4 hours at ambient temperature and the precipitate was filtered off with suction and recrystallised from ethanol. There was obtained 1.2 g. of the title compound; m.p. 249–251° C.

By reaction of 4,4-dimethyl-1,2,3,4-tetrahydro-2-oxo-7-quinolinecarboxylic acid and the mentioned aniline derivatives, the following compounds were prepared analogously to Example 42:

| | designation | yield m.p. | recryst. from |
|---|---|---|---|
| 43 | 4,4-dimethyl-1,2,3,4-tetrahydro-N-(3-trifluoromethylphenyl)-2-oxo-7-quinolinecarboxamide from 3-trifluoromethylaniline | 18% 275–277° C. | ethanol |
| 44 | 4,4-dimethyl-1,2,3,4-tetrahydro-N-(4-cyanophenyl)-2-oxo-7-quinolinecarboxamide from 4-cyanoaniline | 10% 298–301° C. | ethanol |
| 45 | 4,4-dimethyl-1,2,3,4-tetrahydro-N-(4-methoxyphenyl)-2-oxo-7-quiolinecarboxamide from 4-methoxyaniline | 43% 257–259° C. | ethanol |
| 46 | 4,4-dimethyl-1,2,3,4-tetrahydro-N-(4-pyridinyl)-2-oxo-7-quinolinecarboxamide from 4-pyridinamine | 20% 306–309° C. | ethanol |
| 47 | 4,4-dimethyl-1,2,3,4-tetrahydro-N-ethyl-N-phenyl-2-oxo-7-quinolinecarboxamide from N-ethylaniline | 11% 239–241° C. | ethanol |

EXAMPLE 48

2′,3′-Dihydro-N-(3-methoxyphenyl)-2′-oxo-spiro[cyclopentane-1,3′-(1′H)-indole]-6′-carboxamide a) Analogously to Example 1a, from 6′-amino-1′,3′-dihydro-spiro[cyclopentane-1,3′-(2H)-indole]-2′-one there was obtained a yield of 30% of theory of 2′,3′-dihydro-2′-oxo-spiro[cyclopentane-1,3′-(1′H)-indole]-6′-carbonitrile in the form of orange-coloured crystals; m.p. 178–182° C.

b) From this was obtained, analogously to Example 1b, in a yield of 88% of theory, 2′,3′-dihydro-2′-oxo-spiro[cyclopentane-1,3-(1-indole]-6-carboxylic acid in the form of orange-coloured crystals; m.p. 272–276° C.

c) Analogously to Example 1c, there was obtained therefrom, by reaction with 3-methoxyaniline, the title compound in a yield of 34% of theory; m.p. 227° C.

EXAMPLE 49

4,4-Dimethyl-1,2,3,4-tetrahydro-N-(4-fluorophenyl)-2-oxo-7-quinolinecarboxamide was obtained analogously to Example 42 by reaction with 4-fluoroaniline in a yield of 30% of theory; m.p. 281–284° C.

EXAMPLE 50

1-Benzyl-2,3-dihydro-3,3-dimethyl-N-phenyl-2-oxo-(1H)-indole-6-carboxamide was obtained analogously to Example 37 by reaction with benzyl bromide in a yield of 58% of theory; m.p. 84–88° C.

Analogously to Example 1, by reaction with the given amines instead of with aniline, there were obtained the following compounds:

| | designation | yield m.p. | recryst. from |
|---|---|---|---|
| 51 | 2,3-dihydro-3,3-dimethyl-N-(2-pyridinyl)-2-oxo-(1H)-indole-6-carboxamide from 2-pyridinamine | 18% 267–269° C. | ethanol |
| 52 | 2,3-dihydro-3,3-dimethyl-N-(3-pyridinyl)-2-oxo-(1H)-indole-6-carboxamide from 3-pyridinamine | 45% 227–229° C. | ethanol |
| 53 | 2,3-dihydro-3,3-dimethyl-N-(2-chlorophenyl)-2-oxo-(1H)-indole-6-carboxamide from 2-chloroaniline | 48% 235–236° C. | ethanol |
| 54 | 2,3-dihydro-3,3-dimethyl-N-(2-methoxyphenyl)-2-oxo-(1H)-indole-6-carboxamide from 2-methoxyaniline | 30% 221–223° C. | ethyl acetate |
| 55 | 2,3-dihydro-3,3-dimethyl-N-(4-(3-ethoxycarbonylpropyloxy)-phenyl)-2-oxo-(1H)-indole-6-carboxamide from 4-(3-ethoxycarbonylpropyloxy)-aniline | 33% 165–166° C. | ethanol |
| 56 | 2,3-dihydro-3,3-dimethyl-N-(4-chlorophenyl)-2-oxo-(1H)-indole-6-carboxamide from 4-chloroaniline | 66% 249–250° C. | ethanol/ water |
| 57 | 2,3-dihydro-3,3-dimethyl-N-(3-nitrophenyl)-2-oxo-(1H)-indole-6-carboxamide from 3-nitroaniline | 68% 301–303° C. | ethanol/ ethyl acetate |
| 58 | 2,3-dihydro-3,3-dimethyl-N-(2,6-dichlorophenyl)-2-oxo-(1H)-indole-6-carboxamide from 2,6-dichloroaniline | 29% 212–213° C. | ethanol/ water |
| 59 | 2,3-dihydro-3,3-dimethyl-N-(3,5-dichlorophenyl)-2-oxo-(1H)-indole-6-carboxamide from 3,5-dichloroaniline | 60% 261–265° C. | ethanol/ water |
| 60 | 2,3-dihydro-3,3-dimethyl-N-(8-quinolinyl)-2-oxo-(1H)-indole-6-carboxamide from 8-quinolinamine | 59% 269–272° C. | ethanol |
| 61 | 2,3-dihydro-3,3-dimethyl-N-(3,4-dichlorophenyl)-2-oxo-(1H)-indole-6-carboxamide from 3,4-dichloroaniline | 49% 302–304° C. | isopropanol |

Analogously to Example 30, by the reaction of 2,3-dihydro-3,3-dimethyl-2-oxo-(1H)-indole-5-carboxylic acid with the mentioned aniline derivatives, there are prepared the following compounds:

| | designation | yield m.p. | recryst. from |
|---|---|---|---|
| 62 | 2,3-dihydro-3,3-dimethyl-N-phenyl-2-oxo-(1H)-indole 5-carboxamide from aniline | 62% 283–285° C. | ethyl acetate |
| 63 | 2,3-dihydro-3,3-dimethyl-N-(4-fluorophenyl)-2-oxo-(1H)-indole-5-carboxamide from 4-fluoroaniline | 58% 276–278° C. | ethanol |

EXAMPLE 64

2,3-Dihydro-3,3-dimethyl-1-ethyl-N-(4-pyridinyl)-2-oxo-(1H)-indole-6-carboxamide Analogously to Example 35, by reaction with 4-pyridinamine there was obtained the title compound in a yield of 60% of theory; m.p. 209–211° C., after recrystallisation from ethanol/water.

EXAMPLE 65

2,3-Dihydro-3,3-dimethyl-N-(3-aminophenyl)-2-oxo-(1H)-indole-6-carboxamide

Analogously to Example 29, by hydrogenation of the compound of Example 57 there was obtained the title compound in a yield of 95% of theory; m.p. 244–245° C., after recrystallisation from methanol.

EXAMPLE 66

2,3-Dihydro-3,3-dimethyl-N-(4-acetaminophenyl)-2-oxo-(1H)-indole-6-carboxamide 0.83 g. (2.4 mmol) 2,3-Dihydro-3,3-dimethyl-N-(4-aminophenyl)-2-oxo-(1H)-indole-6- carboxamide (from Example 29) was stirred in 5 ml. 2N acetic acid and ml. (53.4 mmol) acetic anhydride for 3 hours at 40° C. The solvent was removed under vacuum and the residue purified by column chromatography (silica gel; isohexane:ethyl acetate:methanol 5:4:0.5 v/v/v) to give 0.6 g. (63% of theory) of the title compound; m.p. 294–295° C.

EXAMPLE 67

2,3-Dihydro-3,3-dimethyl-N-(3-acetaminophenyl)-2-oxo-(1H)-indole-6-carboxamide was obtained analogously to Example 66 in a yield of 73% of theory from the compound prepared in Example 65; m.p. 311–313° C.

EXAMPLE 68

2,3-Dihydro-3,3-dimethyl-(4-butylphenyl)-2-oxo-(1H)-indole-6-carboxamide was obtained analogously to Example 1 by reaction with 4-butylaniline; m.p. 208–210° C.

EXAMPLE 69

2,3-Dihydro-3,3-dimethyl-(4-tert.-butylphenyl)-2-oxo-(1H)-indole-6-carboxamide was obtained in a yield of 78% of theory analogously to Example 1 by reaction with 4-tert.-butylaniline; m.p. 260–263° C.

EXAMPLE 70

2,3-Dihydro-3,3-dimethyl-(4-octylphenyl)-2-oxo-(1H)-indole-6-carboxamide was obtained in a yield of 47% of theory analogously to Example 1 by reaction with 4-n-octylaniline; m.p. 178–180° C.

EXAMPLE 71

2,3-Dihydro-3,3-dimethyl-N-(4-methoxycarbonylphenyl)-2-oxo-(1H)-indole-6-carboxamide was obtained in a yield of 50% of theory analogously to Example 1 by reaction with methyl 4-aminobenzoate; m.p. 258–260° C.

EXAMPLE 72

2,3-Dihydro-3,3-dimethyl-N-(3-ethoxycarbonylpropoxyphenyl)-2-oxo-(1H)-indole-6-carboxamide was obtained in a yield of 48% of theory analogously to Example 1 by reaction with ethyl 3-(3-aminophenyloxy)butanoate; m.p. 96–98° C.

EXAMPLE 73

2',3'-Dihydro-N-phenyl-2'-oxo-spiro[-yclopentane-1,3'-(1'H)-indole]-6'-carboxamide was obtained in a yield of 40% of theory analogously to Example 48 by reaction with aniline; m.p. 249° C.

Pharmacological Test Results

Erythrocyte aggregation was determined with a mini-erythrocyte aggregometer of the firm Myrenne, Rotgen (see Kiesewetter et al., Biomed. Tecknik, 27, 209–213/1982). This apparatus produces as the test result a dimensionless index which increases with increasing aggregation tendency of the tested compound. The investigations were carried out with human blood from healthy donors. The blood was adjusted to a haematocrit of 45% and incubated with a control solution or with a solution of a test substance. The erythrocyte aggregation was then measured. Each compound was investigated at a concentration of $10^{-5}$ molar. Two investigations with the blood from two donors were conducted for each compound. The difference of the aggregation indices ( E) between the initial value of the control solution and the values with the solutions of the test compounds was calculated.

In the following Table, the findings obtained for the erythrocyte aggregation (E) are set forth. The lower a given value of (E), the more effective is the test compound. In comparison, venoruton, a mixture of various $0\text{-}(\beta\text{-hydroxyethyl})$rutosides, at a comparable concentration of $1.7 \times 10^{-5}$ M, only brings about a change of the erythrocyte aggregation index of $-0.4$. Even at a concentration of $1.7 \times 10^{-3}$ M, the change produced by venoruton, which is reported to inhibit the tendency towards erythrocyte aggregation (see Schmid-Schonbeim et al., VASA, 4, 263–270/1975), only amounts to $-3.9 \pm 0.9$.

In comparison with the prior art, the compounds of the present invention clearly more strongly inhibit erythrocyte aggregation.

| Inhibition of the erythrocyte aggregation (E) | |
|---|---|
| Compound of example | E |
| 1 | −14 |
| 2 | −12 |
| 3 | −11 |
| 4 | −10 |
| 8 | −11 |
| 12 | −9 |
| 14 | −9 |

We claim:
1. A compound of the formula:

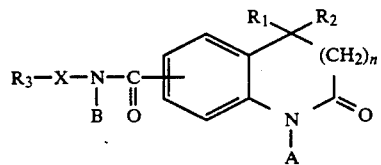

wherein A is a hydrogen atom or a $C_1$–$C_6$-alkyl, $C_2$–$C_6$-alkenyl, $C_2$–$C_6$-alkynyl, benzyl or $C_3$–$C_7$-cycloalkyl radical, B is a hydrogen atom, $R_1$ is a $C_1$–$C_6$-alkyl, $C_2$–$C_6$-alkenyl, or $C_3$–$C_7$-cycloalkyl radical, $R_2$ is a $C_1$–$C_6$-alkyl, $C_2$–$C_6$-alkenyl, $C_3$–$C_7$-cycloalky, $C_1$–$C_6$-alkylcarbonyl, $C_1$–$C_6$-alkoxycarbonyl, aminocarbonyl or hydrazinocarbonyl radical or $R_1$ and $R_2$, together with the carbon atom to which they are attached, form a $C_3$–$C_7$-cycloalkyl ring, n is 0, X is a valency bond or a $C_1$–$C_6$-alkylene radical, $R_3$ is a phenyl ring of the formula:

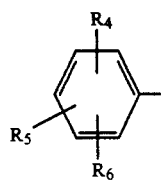

wherein $R_4$, and $R_5$ and $R_6$ can be the same or different and each signifies a hydrogen atom, $C_1$–$C_6$-alkanesulphonyloxy, trifluoromethanesulphonyloxy, phenylsulphonylamino, $C_1$-$C_6$-alkanesulphonylamino, trifluoromethanesulphonylamino, N-$C_1$-$C_6$-alkyl-alkanesulphonylamino, N-$C_1$-$C_6$-alkyl-trifluoromethanesulphonylamino, $C_1$-$C_6$-alkylsulphenylmethyl, $C_1$-$C_6$-alkylsulphinylmethyl or $C_1$-$C_6$-alkyl-sulphonylmethyl radical, a carbonyl group substituted by hydroxyl, $C_1$-$C_6$-alkoxy, $C_1$-$C_6$-alkylamino or di-$C_1$-$C_6$-alkylamino, a sulphonyl group substituted by amino, $C_1$-$C_6$-alkylamino or di-$C_1$-$C_6$-alkylamino, a $C_1$-$C_6$-alkylcarbonylamino, aminocarbonylamino, $C_1$-$C_6$-alkylaminocarbonylamino, $C_1$-$C_6$-alkylthio, $C_1$-$C_6$-alkylsulphinyl, $C_{1-6}$-alkylsulphonyl, nitro, halogen, amino, hydroxy, $C_1$-$C_8$-alkyl, $C_1$-$C_6$-alkoxy, $C_2$-$C_6$-alkenyloxy, $C_2$-$C_6$-alkynyloxy, cyano-$C_1$-$C_6$-alkoxy, carboxy-$C_1$-$C_6$-alkoxy, $C_1$-$C_6$-alkoxycarbonyl-$C_1$-$C_6$-alkoxy, di-$C_1$-$C_6$-alkylamino, trifluoromethyl or cyano group, or $R_3$ is a naphthyl, tetrahydronaphthyl, biphenyl, methylenedioxyphenyl or ethylenedioxyphenyl radical; and the tautomers, optically-active forms or a physiologically acceptable salts thereof with organic and inorganic acids.

2. A compound according to claim 1, wherein A is a hydrogen atom or a benzyl, $C_1$-$C_6$-alkyl or $C_2$-$C_4$-alkenyl radical.

3. A compound according to claim 1 or 2, wherein $R_1$ and $R_2$ are each independently $C_1$-$C_4$-alkyl radicals or $R_1$ and $R_2$ together represent a $C_5$-$C_6$-cycloalkyl ring.

4. A compound according to claim 1 or 2, wherein $R_3$ is a phenyl radical which is unsubstituted or substituted by $C_1$-$C_4$-alkylsulphonyloxy, trifluoromethanesulphonyloxy, $C_1$-$C_4$-alkylsulphonylamino, trifluoromethanesulphonylamino, $C_1$-$C_4$-alkylthio, $C_1$-$C_4$-alkylsulphinyl, $C_1$-$C_4$-alkynyloxy, hydroxyl, $C_1$-$C_8$-alkyl, $C_1$-$C_4$-alkoxy, $C_2$-$C_4$-alkynyloxy, trifluoromethyl, $C_2$-$C_4$-alkenyloxy, $C_1$-$C_4$-alkoxycarbonyl-$C_1$-$C_4$-alkoxy, nitro, amino, $C_1$-$C_4$-alkylcarbonylamino, $C_1$-$C_4$-alkoxycarbonyl, chlorine, fluorine, cyano or di-$C_1$-$C_4$-alkylamino, or $R_3$ is a methylenedioxyphenyl, ethylenedioxyphenyl, naphythyl, tetrahydronaphthyl or biphenyl radical.

5. A compound according to claim 1 or 2, wherein the $R_3$—X—N(B)—CO— radical is in the 5- or 6-position of the oxindole ring.

6. A compound according to claim 1 or 2, wherein $R_1$ and $R_2$ are each methyl radicals, and X is a valency bond.

7. Pharmaceutical composition containing at least one compound according to claim 1 and a pharmaceutically acceptable carrier.

8. A method of inhibiting the aggregation of erythrocytes or thrombocytes in a patient in need of such inhibition, said method comprising administering to the patient an inhibiting amount of a compound of claim 1 or 2.

9. A compound of the formula:

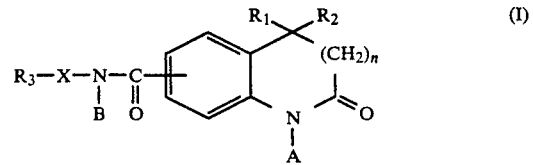

wherein A and B are hydrogen; $R_1$ and $R_2$ are $C_1$-$C_6$-alkyl; n is 0; X is a valency bond, and $R_3$ is (a) phenyl, which is unsubstituted or substituted by halogen, trifluoromethyl, methoxy, methyl, or hydroxy.

10. A compound of claim 9, wherein said compound is selected from the group consisting of 2,3-dihydro-3,3-dimethyl-N-phenyl-2-oxo-(1H)-indole-6-carboxamide;
2,3-dihydro-3,3-dimethyl-B-(3-trifluoromethyl-phenyl)-2-oxo-indole-6-carboxamide;
2,3-dihydro-3,3-dimethyl-N-(4-hydroxy-2-methyl-phenyl)-2-oxo-(1H)-indole-6-carboxamide;
2,3-dihydro-3,3-dimethyl-N-(4-fluorophenyl)-2-oxo-(1H)-indole-6-carboxamide; and
2,3-dihydro-3,3-dimethyl-N(3-methoxyphenyl)-2-oxo-(1H)-indole-6-carboxamide.

* * * * *

UNITED STATES PATENT AND TRADEMARK OFFICE
CERTIFICATE OF CORRECTION

PATENT NO. : 5,019,587

DATED : May 28, 1991

INVENTOR(S) : Wolfgang Von Der Saal

It is certified that error appears in the above-identified patent and that said Letters Patent is hereby corrected as shown below:

On the cover page, Item [75], first inventor, "Wolfgang V. Von Der Saal" should read --Wolfgang Von Der Saal--.

Signed and Sealed this

Fifth Day of January, 1993

Attest:

DOUGLAS B. COMER

*Attesting Officer*     *Acting Commissioner of Patents and Trademarks*